(12) United States Patent
Allgeyer

(10) Patent No.: US 6,196,225 B1
(45) Date of Patent: Mar. 6, 2001

(54) ENDOTRACHEAL TUBE FOR USE DURING FIBEROPTIC ASSISTED INTUBATION AND WITH OTHER INTUBATING STYLETS

(76) Inventor: Dean O. Allgeyer, 762 Glenmont Ave., Los Angeles, CA (US) 90024

(*) Notice: Subject to any disclaimer, the term of this patent is extended or adjusted under 35 U.S.C. 154(b) by 519 days.

(21) Appl. No.: 08/645,144

(22) Filed: May 13, 1996

Related U.S. Application Data

(63) Continuation-in-part of application No. 08/546,681, filed on Oct. 23, 1995, now abandoned.

(51) Int. Cl.[7] ................................................ A61M 16/00
(52) U.S. Cl. ............................. 128/207.15; 128/200.26
(58) Field of Search ...................... 128/200.26, 207.14, 128/207.15

(56) References Cited

U.S. PATENT DOCUMENTS

| | | |
|---|---|---|
| 3,964,488 | 6/1976 | Ring et al. . |
| 3,968,800 | 7/1976 | Vilasi ............................. 128/207.14 |
| 4,041,936 | 8/1977 | Carden . |
| 4,166,468 | 9/1979 | Haynie ............................ 128/207.15 |
| 4,846,153 | 7/1989 | Berci .............................. 128/200.26 |
| 4,977,894 | 12/1990 | Davies ........................... 128/207.15 |
| 5,016,614 | 5/1991 | MacAllister .................... 128/200.26 |
| 5,285,778 | 2/1994 | Mackin ........................... 128/207.15 |
| 5,329,940 | 7/1994 | Adair ............................. 128/200.26 |
| 5,400,771 | 3/1995 | Pirak et al. ..................... 128/200.26 |

OTHER PUBLICATIONS

*Mercury Medical Anesthesia Desk Reference* (1993) Cover & p. 52.
Catalog cut of Olypmus Tracheal Intubation Fiberscope depicting fiberscope & endotracheal tube.
Advertisement for retrograde intubation products sold by Cook Critical Care.
*Anesthesia & Analgesia*, vol. 78, No. 4, Brull et al, pp. 746–748, "Facilitation of Fiberoptic Orotracheal . . . "
*Fiberoptic Airway Endoscopy in Anesthesia & Critical Care*, by Andranik Ovassapian, Chap. 5, "Fiberoptic Tracheal Intubation".
*Airway Management: Principles & Practice*, J.L. Benumof, ed. (1996), Chap. 16, pp. 282–318,"Fiberoptic Endoscopy–Aided Techiques".

*Primary Examiner*—Aaron J. Lewis
(74) *Attorney, Agent, or Firm*—Fulwider Patton Lee & Utecht, LLP

(57) ABSTRACT

An endotracheal tube for use with a fiberoptic bronchoscope or other intubation stylet is described. There are ventilation holes located on the tapering section on the distal tip such that ventilation may occur while using the fiberoptic scope and such that resistance to ventilation is minimized with the scope removed. The endotracheal tube is particularly useful for difficult intubations as the distal tip is tapered which facilitates passage through the larynx.

5 Claims, 3 Drawing Sheets

ENDOTRACHEAL TUBE FOR USE DURING FIBEROPTIC ASSISTED INTUBATION AND WITH OTHER INTUBATING STYLETS

This application is a continuaton-in-part of Ser. No. 08/546,681 filed Oct. 23, 1995 now abandoned.

BACKGROUND OF THE INVENTION

This invention relates to medical equipment used in the fields of anesthesiology and emergency airway management. More particularly, the invention relates to an endotracheal tube used in conjunction with a fiberoptic bronchoscope, or other stylet, to overcome intubation difficulties.

Provision of anesthesia to patients during surgical procedures requires ensuring adequate respiratory function. This is most often accomplished by use of an endotracheal tube (ETT). Placement of an endotracheal tube for support of respiration is a critical step in the provision of anesthetic patient care. Placement of the ETT is performed most often under direct visualization using a laryngoscope. However, this procedure can be difficult to accomplish due to anatomic anomalies. Often, a fiberoptic bronchoscope (FOB), or other intubating stylet, is used to overcome these instances of difficult intubations. Use of an FOB allows visualization of the upper airway structures and visual confirmation that the trachea has been entered. Once the trachea has been entered, the FOB is used as a stylet guide to place an ETT. The ETT is slid over the FOB into the trachea. Once the ETT has been successfully placed in the trachea, the FOB is withdrawn and the patient can be ventilated. Other types of stylets are also known.

The currently utilized ETTs were originally designed for intubation under direct visualization and without consideration of use in conjunction with an FOB or other intubating stylet. Their design incorporates a constant diameter tube with a leading edge. When using a standard ETT over an FOB, or other intubating stylet, the leading edge can become impacted on the laryngeal structures causing trauma, delay, or failed intubation.

Endotracheal tubes are in general flexible breathing conduits constructed of medical grade plastics that are adapted to be placed in the patient's trachea. The proximate end of the ETT has a standard fitting allowing connection to a source of pressurized gas such as oxygen and anesthetic gases. The distal end is open to deliver these gases to the trachea and lungs of the patient. The distal end usually has a side hole to aid in equal ventilation of both lungs should the ETT be inaccurately positioned. This side hole is not intended to, nor does it, decrease ventilatory resistance in an ETT that is correctly positioned. The ETT typically has an inflatable bladder or balloon which can be inflated once the ETT is in place within the trachea. This seals the trachea allowing positive pressure ventilation to the lungs and protecting them from secretions and gastric contents. During the intubation process the ETT traverses the mouth, pharynx, larynx, and trachea of the patient and is ultimately placed in the correct position within the trachea without causing damage to bodily structures. Various devices are available to assist with this process, the most important of them being the fiberoptic bronchoscope.

An FOB consists of three basic parts, a proximal control assembly which includes an eyepiece for viewing, an elongated shaft housing fiberoptic bundles, channels, and control wires, and a distal tip containing optics . In use, a high intensity light source is connected via the proximal control assembly for transmission through the fiberoptic bundles. The fiberoptic bundles transmit the light to the distal tip where it is used to illuminate the object to be viewed. Optics located in the distal tip transmit the image through another fiberoptic bundle to the proximal control assembly where the image can be viewed with ones eye or transmitted to a TV monitor for viewing.

In certain situations an FOB is used in conjunction with an ETT to intubate a difficult airway. This is sometimes anticipated prior to anesthetizing a patient but more often is an emergency procedure in a patient who is discovered to have a difficult airway after being anesthetized. In either situation, an appropriate size ETT for the patient is chosen and threaded onto the proximal shaft of the FOB. The tip is of the ETT is lubricated with a water soluble medical lubricant. The procedure for using an FOB as an intubating stylet is the same whether one is using a standard ETT or the described tapered ETT. The upper airways are traversed with the distal tip of the FOB and the laryngeal structures are visualized and identified. The distal tip of the FOB is advanced through the vocal cords and into the trachea. Once entrance of the FOB into the trachea is visually confirmed, the ETT is slid down the shaft of the FOB, using the FOB as an intubating stylet. The tip of the ETT must traverse the larynx prior to entering the trachea, and it is at this point resistance and obstruction to advancement is not infrequently encountered. Thereafter the ETT must be positioned accurately within the trachea and is done so either by direct visualization of the bronchi and carina (the first division of the trachea) through the FOB, or by using predetermined norms for ETT position and listening to breath sounds. Once positioned and the tracheal balloon inflated, the FOB is removed from the ETT. The proximal end of the ETT is then connected to a pressurized gas source and the patient is ventilated.

Trauma from ETT placement may cause bleeding, swelling, laryngospasm, patient discomfort and hoarseness. Delayed or failed intubation can cause brain damage and/or death. This cause of delayed, traumatic, or failed intubation when using an FOB/ETT combination is not infrequent and is documented in the anesthesia literature. For example, Ovassapian states: "In 20–30% of patients, even though the fiberscope has entered the trachea, the endotracheal tube impinges on the larynx and cannot be advanced into the trachea. It is postulated that the tube catches on the epiglottis or on the vocal cords or that it lodges in the pyriform sinus."

Benumof states: "The free lumen of the endotracheal tube predisposes the tube to move away from the the insertion cord of the FOB and catch the laryngeal structures, therefore interfering with the smooth entrance of the tube into the trachea." Brull et al report that fully 13 of 20 FOB assisted intubations using a standard ETT were unsuccessful on the first attempt. Moreover, 7 of 20 patients were unable to be intubated using this technique (standard ETT over an FOB) on the third attempt. They state: "Furthermore, repeated attempts at passage may result in airway bleeding, damage to the arytenoid cartilages or epiglottis, or swelling of the airway, making subsequent endotracheal intubations attempts more difficult." Failed intubation is a significant cause of anesthetic related brain damage, death, and malpractice litigation.

The same problem has been described when using standard ETT's over other intubation stylets. The problem is most severe in the instance of retrograde intubation. Retrograde intubation involves placing a guide wire through the crico-thyroid membrane and bringing it out through the patient's mouth. The wire is then used as a stylet guide for an ETT. Because of the relatively large discrepancy between the thin wire (0.038-inch outer diameter) and the ETT (7–8 millimeters internal diameter), the tip of the ETT often impinges upon the larynx.

Several ETTs and other devices have been designed for specific functions and to overcome specific difficulties related to the difficult airway. For example, Ring, Adair, and Elwyn, in U.S. Pat. No. 3,964,488, seek to overcome the problems of ETT kinking and obstruction by incorporating a preformed angle in the shaft of an ETT. Carden, in U.S. Pat. No. 4,041,936, describes an ETT designed for use during fiberoptic bronchoscopy of the lungs which simplifies the procedure. Vilasi, in U.S. Pat. No. 3,968,800 describes a "Device For Insertion Into A Body opening." One embodiment is an endotracheal tube with an adjustable external circumference which seeks to overcome the need to stock multiple size ETTs and to supplant the need for a tracheal balloon. Adair, in U.S. Pat. No. 5,329,940 describes an "Endotracheal Tube Intubation Assist Device" which couples an FOB with a television monitor to assist with the problem of difficult intubation. Cook Medical markets a retrograde intubation kit, which also seeks to address the problem of the difficult airway.

Vilasi describes a device which generally suffers from complexity, and is therefore more expensive to manufacture, is more user dependent in its correct operation and application than a simpler device, and is more time consuming to operate than a simpler device designed for the same purpose. Using this device as an ETT would raise safety issues as well. One can see that an FOB placed through this device in the non-expanded configuration would significantly interfere with ventilation. This is a serious drawback of the design for use with an FOB, as the ability to visualize anatomic structures while maintaining sufficient ventilation is often necessary or desirable, such as when one is checking for corret placement of the ETT within the trachea. This is accomplished by using an FOB bronchoscopy adaptor which allows the FOB and pressurized gases to be delivered through the ETT at the same time. Attempting to intubate a patient or position the device by moving it in the expanded configuration (intentionally or unintentionally), within the trachea, would risk laceration of the trachea or other upper airway structures, a potentially disastrous complication. Using the device of Vilasi in solelynhe closed configuration would be limited by the increase in resistance to gas flow caused by narrowing the distal end according to Poiseuille's law which states resistance is inversely proportional to the inside radius of the conduit to the 4th power. Hence, small decreases in ETT size give large increases in airway resistance. Therefore, the more useful the device of Vilasi is for intubating difficult airways over a stylet, the less useful the device becomes as a breathing conduit due to the increase in airway resistance.

Adair utilizes a standard ETT in conjunction with his device for assisted intubations. The standard ETT depicted in Adair is not tapered, has a leading edge, and an opening at the distal end which aids in the equal dispersion of oxygen into the lungs. Its use with a standard ETT is therefore subject to the same problems described above, stemming from size discrepancy and the leading edge.

Others in the art teach using a standard ETT for instances when an intubating stylet of one type or another are used. Examples of intubating stylets include FOB's, tracheal tube changers, tracheal tube introducers and guides, and wires used in retrograde intubation kits. For example, the ETT illustrated in the retrograde intubation and tracheal tube changer literature is of standard design. Olympus, the leading FOB manufacturer, depicts a standard ETT in their literature.

The problem of the tube tip catching on the laryngeal structures is in part a function of the discrepancy between the diameter of the intubating stylet and the ETT, causing the leading edge to be oriented incorrectly as the distal tip approaches the larynx. Attempts to overcome this problem have been made. For example, Cook Medical includes an obturator sheath which functions as a spacer in its retrograde intubation kit. The spacer is fitted over the wire after a retrograde intubation wire has been placed, after which the ETT is slid down the combined wire/spacer assembly. This adds another step and time to a procedure in which time is of the essence but is deemed necessary to address the size discrepancy problem. It also does not necessarily solve the problem, only lessens it by degree. Brull et al. describe having greater success using a spiral wound, more flexible ETT than a standard ETT for fiberoptic assisted intubations. They postulate that improved performance was due to the increased flexibility of the ETT, and to a less acute angle of the leading edge relative to the longitudinal axis of the ETT as opposed to the standard ETT. They also note that the Spiral Wound ETT was 10–20 times the cost of a standard ETT and that 5% of the time intubation using the spiral wound ETT and an FOB was unsuccessful in their series. The described ETT of the present invention represents an improvement over the prior art for this purpose.

SUMMARY OF THE INVENTION

The objectives of the invention are accomplished by providing a distally tapering endotracheal tube, with no significant leading edge, that has ventilation holes placed on the tapering portion of the ETT to mitigate what would otherwise be a prohibitive increase in the resistance to gas flow. Additionally, the tube is typically constructed of polyvinyl chloride and otherwise manufactured in the same fashion as a standard ETT. The tapered ETT may be constructed of various sizes to match patient needs. Similarly, the distal aperture for passage of the FOB may be of various sizes to complement the diameter of the FOB in use. The ideal aperture would be only slightly larger in diameter than the FOB in use, such that the ETT slides easily upon the shaft of the FOB yet is closely contoured to the shaft in order to prevent difficulty of passage of the ETT at the level of the larynx. The ventilation holes are distal to the tracheal balloon and are preferrably placed mainly or wholly on the tapered portion of the ETT. This allows adequate ventilation when the FOB is in use and protruding through the distal aperture. Ventilation is accomplished by attaching a fiberoptic bronchoscopy adaptor to the proximate end of the ETT which allows connection to a pressurized gas source and passage of an FOB through a diaphragm.

This new feature can be critical in the following situations. Difficult intubations are those instances most likely to lead to aspiration of gastric contents into the lung. This will cause hypoxemia with its attendant problems of cardiovascular instability and brain damage if not reversed. Aspiration is best diagnosed by viewing the bronchi with an FOB, looking for bile, food particles, and erythema. While one is interested in making the diagnosis rapidly in order to institute the correct therapy, one does not want to interrupt ventilation which will exacerbate hypoxemia. Additionally, when hypoxemia occurs, one of the first maneuvers is to check for correct placement of the ETT, as misplacement is a frequent cause of hypoxemia. This ETT will allow continued ventilation while the FOB is in use and will address this dilemma.

With the FOB removed from the ETT, the combination of side holes and the distal aperture provide for ventilation through the ETT without a significant increase in ventilatory resistance relative to a standard ETT. Thus, this invention accomplishes the objectives of making difficult intubations safer, less traumatic, and quicker when using this ETT in conjunction with an FOB or intubating stylet, but without a significant increase in ventilatory resistance that would otherwise limit its usefulness. Additionally it allows ventilation through a tapered ETT while the FOB is in use and so has the added feature of combined ventilatory support and diagnostic capacity.

Accordingly, there are several objects and advantages of my invention.

One advantage provides an endotracheal tube that when used in conjunction with a fiberoptic bonchoscope, or other intubating stylet, will result in safer intubations.

Another provides an endotracheal tube that when used in conjunction with a fiberoptic bronchoscope, or other intubating stylet, will result in less trauma to the airway during intubation.

Yet another benefit of my invention is to provide an endotracheal tube that when used in conjunction with a fiberoptic bronchoscope will result in fewer instances of failed intubations.

Yet another benefit of my invention is to provide an ETT that when used in conjunction with an FOB or other intubation stylet will result in quicker intubations.

Another benefit of my invention is to provide an endotracheal tube that will facilitate intubations over an FOB or intubating stylet yet will not significantly increase resistance to ventilation when the ETT is in use with the FOB or stylet removed.

Another benefit of my invention is to accomplish the above goals by providing an ETT which is simple to use and cost effective to manufacture.

Further objects and advantages of this invention will become apparent from a consideration of the drawings and ensuing description.

BRIEF DESCRIPTION OF THE DRAWINGS

In the drawings, closely related figures have the same number but different alphabetic suffixes.

PREFERRED EMBODIMENT OF THE INVENTION

Figure 1A:
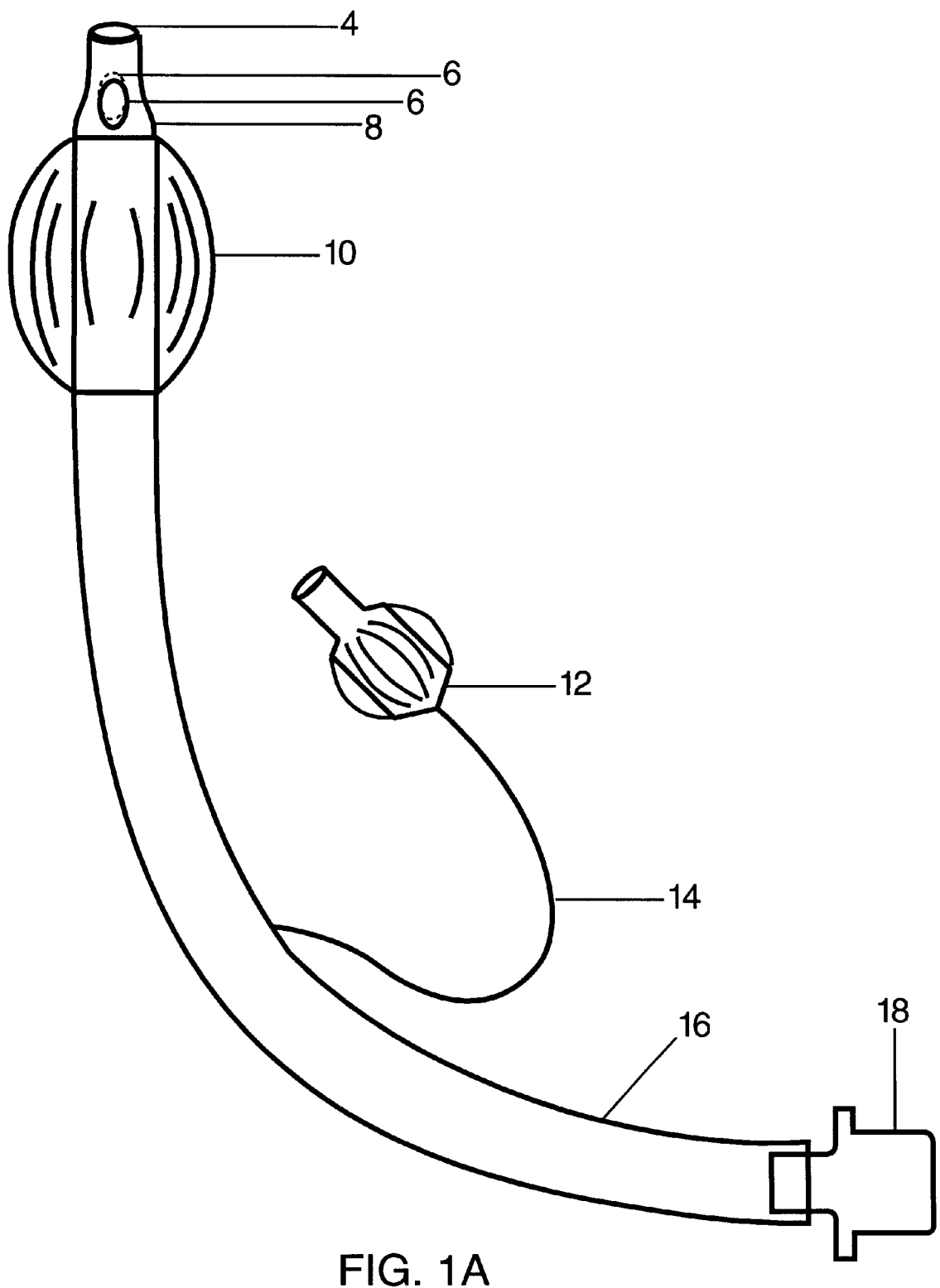
FIG. 1A is a perspective view of the endotracheal tube.
Figure 1B:
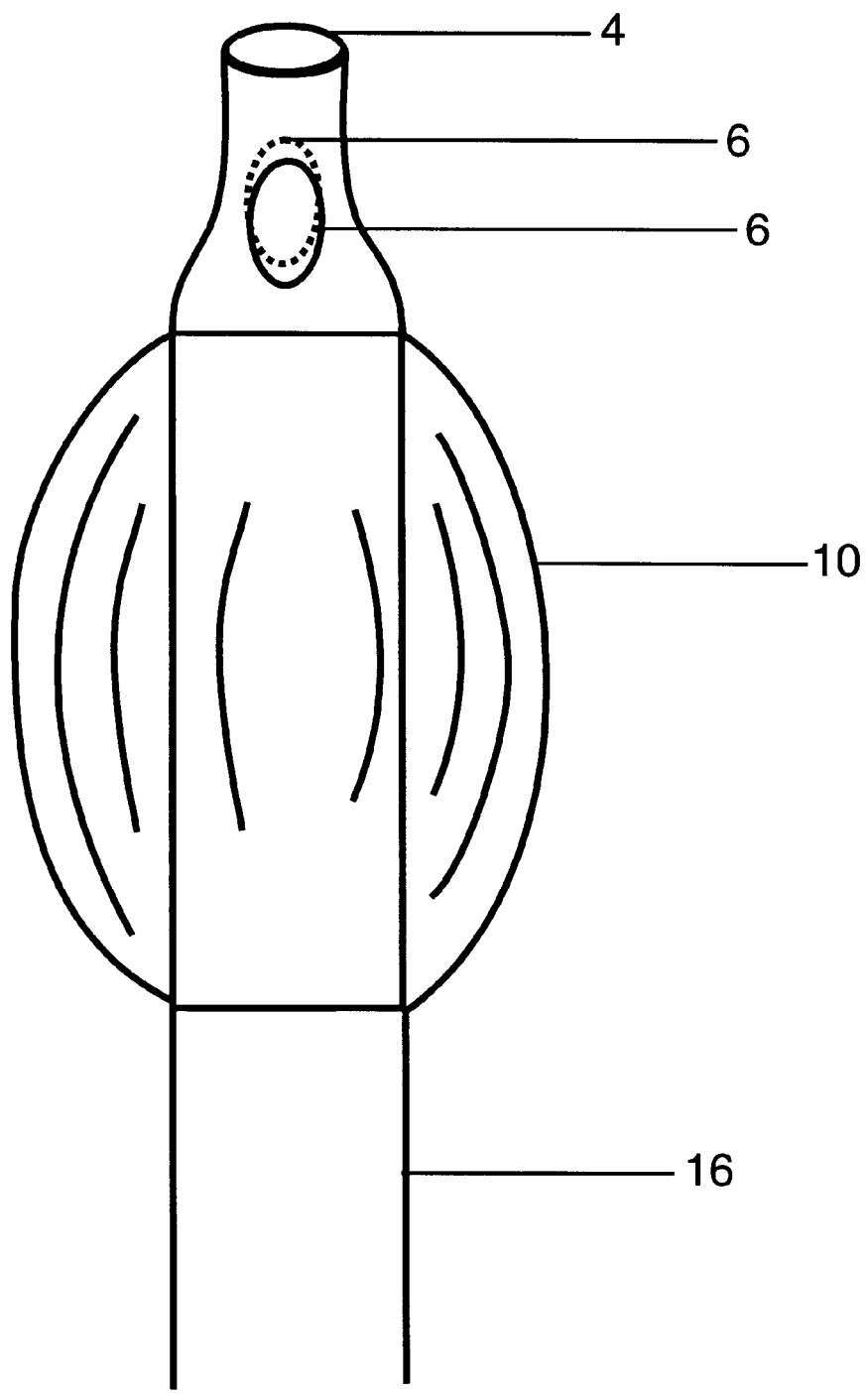
FIG. 1B is a detailed drawing of the distal end of the ETT showing the novel features of the invention in a perspective view.
Figure 2:
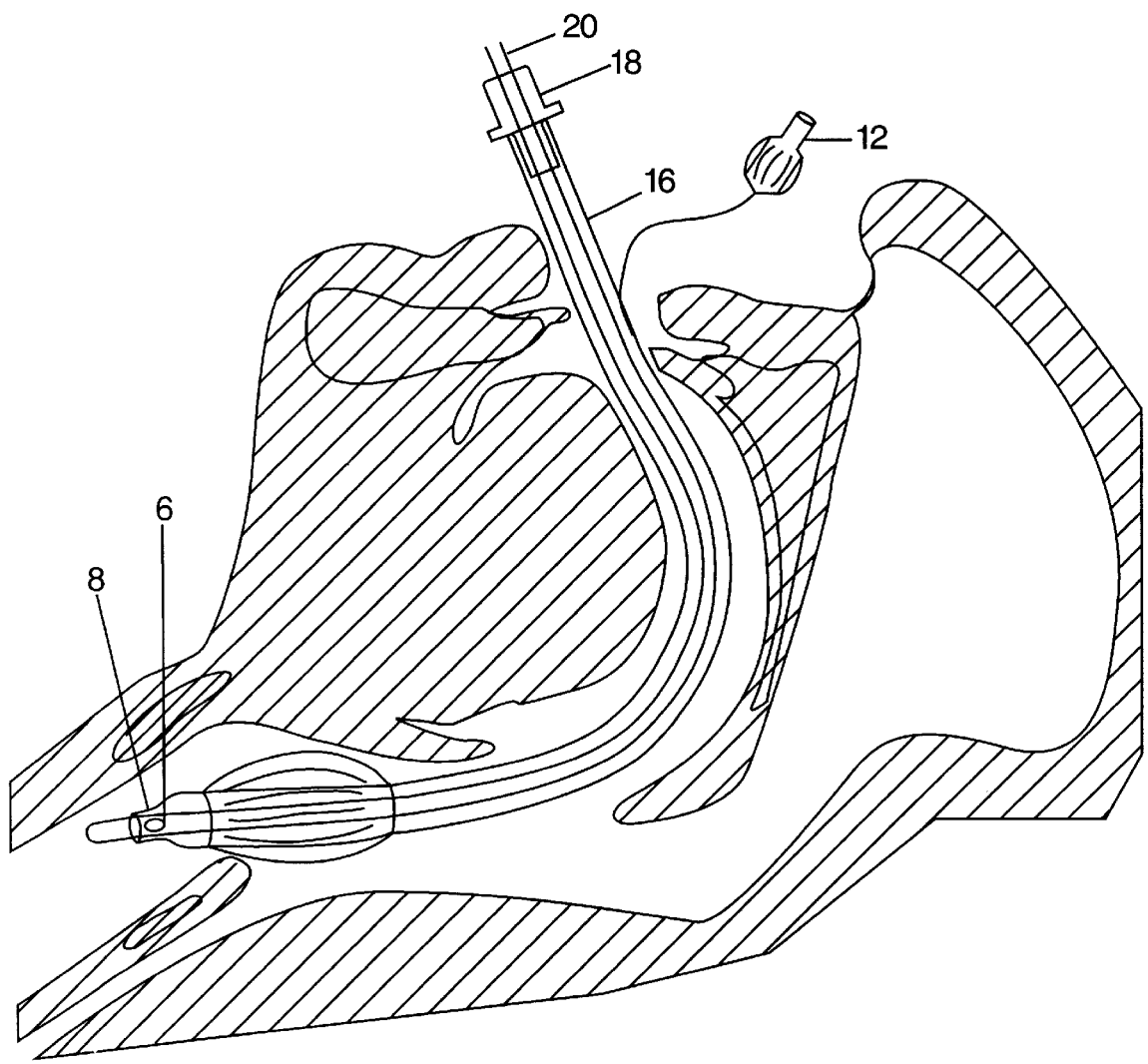
FIG. 2 is a cross section of a human head showing the endotracheal tube in use with a fiberoptic bronchoscope (the proximal control and eyepiece assembly is not shown).

Referring now to FIGS. 1–2, an endotracheal tube 16 for use during fiberoptic assisted intubations and with other intubating stylets is shown. The manner of using the tapered ETT 16 utilizes the same technique now being used with conventional ETT's for FOB assisted intubation of the trachea. Specifically, one first places the shaft of the FOB 20 (proximal control assembly not shown) through the lumen of the ETT 16. Standard features incorporated include a pilot balloon 12 that communicates with a tracheal balloon 10 via tubing 14. The combined apparatus is placed in the pharynx and the laryngeal structures are visually identified with the FOB 20. The FOB 20 is passed through the vocal cords into the trachea under bronchoscopic visualization. The ETT 16 can now be slid down the shaft of the FOB 20 into the trachea using the shaft of the FOB 20 as a stylet guide as depicted in FIG. 2. This last maneuver is often where difficulty is encountered with a conventional ETT due to its non-tapered shape and leading edge. Not uncommonly, the leading edge will impinge on the laryngeal structures. This may cause trauma, and or delay, and or abandonment of the procedure. The tapered tip 8 of the described ETT is less traumatically and more quickly placed, with greater success rates due to the combination of (a) a smaller diameter distal end 8 which is more closely contoured to the shaft of the FOB 20, and (b) the absence of a leading edge. A tapered tip should be understood as a structure whose distal end is significantly smaller in diameter than that of the tube. There is no precise dimensional relationship between the tube and distal end diameters, although an example is provided below. The emphasis here is in avoiding a leading edge and in reducing the size of the ETT'S distal end so that the previously discussed problems are minimized or eliminated, all while still providing respiratory function with no complicating resistance.

The ventilation holes 6 situated on the tapering portion of the ETT allow ingress and egress of respiratory gases without undue resistance to flow. They do so by a) increasing the cross sectional area available for passage of respiratory gases, and b) when the ETT 16 is in place within the trachea, by allowing enough clearance between the tracheal wall and the ventilation holes 6 such that gas exchange is not significantly impeded. Placing the ventilation holes 6 on the tapered portion of the distal end 8, as opposed to the non-tapered portion of the ETT 16 distal to the balloon 10, also removes the holes 6 from the proximity of the balloon 10 and thus the possibility of obstruction due to balloon 10 herniation. Less preferred embodiments place the holes 6 partially on or just off the tapered portion of the tube. Herniation can occur when the balloon 10 covers and thus obstructs ventilation through holes 6 due to overexpansion. All functions that may be performed with a conventional ETT, e.g. passage of a suction catheter or application of positive end expiratory pressure, can be performed with the ETT 16. Additionally, ventilation can be performed through the holes 6 while the FOB 20 is in use and protruding through, and therefore obstructing, the distal aperture 4. This would be impossible with a standard, non-tapered ETT whose internal diameter is only slightly greater than the FOB 20.

A preferred embodiment of a fiberoptic endotracheal tube 16 is illustrated in FIG. 1A. A standard universal adaptor 18 is seated into a unitary endotracheal tube 16. The ETT 16 is manufactured by a plastic injection technique using a soft medical grade polymer such as polyvinyl chloride in the same fashion as are standard ETT's. The most useful sizes for the ETT 16 (in adults) are from 6.5 mm to 8.5 mm internal diameter, increasing in 0.5 mm increments. FOB 20 are manufactured with a variety of standard shaft sizes, 3.7 or 4.0 mm diameter being the most versatile and common for adults. Therefore, for example, with a 3.7 mm FOB 20 protruding through the distal aperture 4, of a 8.0 mm ETT 16, fully 79 percent of the cross sectional luminal area of the non-tapered portion of the ETT 16 remains available for ventilation. The remaining cross sectional luminal area is 39.5 square millimeters, which is slightly greater than a standard 7.0 ETT (38.47 square millimeters). Endotracheal tubes for pediatric use, for example, would be proportionately smaller.

Utilizing an ETT with a distal aperture 4 approximately 0.3 mm in diameter greater than the FOB 20 used as a stylet allows for smooth action of the ETT 16 upon the FOB 20. Therefore, for use with a 3.7 mm FOB, the distal aperture 4 can be manufactured with an internal diameter of 4 mm. One can see, for example, using an ETT 16 of standard internal diameter 8.0 mm allows a 50% reduction in distal aperture 4 internal diameter relative to a non-tapered ETT. These dimensions are by way of example only. They are subject to variance based upon preferences of manufacturers and physicians. The principle requirement in the different diameters of the ETT and the FOB is smooth action between the two.

The distance from the distal tip of the ETT 16 to the distal border of the balloon 10 when inflated is variable and is a function of style of taper employed, i.e. straight or nipple shape. In general the distance is approximately 22 mm, which is currently utilized in a standard adult ETT.

FIG. 1B is a detailed illustration including the features of this invention in a preferred embodiment. The distal tapered end 8 is shown terminating in a circular aperture 4 which is oriented perpendicular to the long axis of the endotracheal tube. Therefore, the ETT 16 does not have a leading edge. The ventilation holes 6 are situated on the tapering portion of the distal tapered end 8.

FIG. 2 is an illustration of the endotracheal tube 16 in use with a fiberoptic bronchoscope 20 (control and eyepiece assembly not shown), during the intubation process.

While my above description contains many specificities, these should not be construed as limitations on the scope of the invention, but rather as an exemplification of one preferred embodiment thereof. Many other variations are possible. For example, the distal aperture 4 need not be perfectly perpendicular to the long axis of the ETT and consequently need not be perfectly circular. The ETT itself need not be perfectly circular for that matter and could be elliptical, for example. The requirement is there not be a significant leading edge such that there is a risk of the leading edge impinging on the larynx with regularity. The aperture 4 may be of various sizes and shapes. The tapered end 8 can be of various shapes as opposed to the mammalian nipple shape shown in the drawings. It could be, for example, a truncated conical section, with or without a generally cylindrical, short guide at the very tip of the taper.

The ventilation holes 6 can be of various number, size, shapes, and locations, etc., so long as the structural integrity of the ETT is maintained. Thus, for example, there could be two, three, or four holes on the tapered portion. Those holes could be circular, elliptical, or even triangular. In the instance where the tapered tip comprised a mammalian nipple, the hole may even be located on an untapered portion of the nipple. Still another embodiment of the invention contemplates that the ventilation holes are disposed on the constant diameter portion of the ETT, between the tracheal balloon and the tapered tip. Thus the scope of the invention should be determined by the appended claims and their legal equivalents, rather than by the examples given.

What is claimed is:

1. An endotracheal tube, adapted for use with a fiberoptic bronchoscope or other intubating stylet, for facilitating intubation and decreasing the likelihood of laryngeal impingement, comprising:

a) a tracheal balloon;

b) a unitary tube, passing through said balloon, and having a portion of generally constant cross section disposed on a proximal side of said balloon;

c) a tapered end portion of said unitary tube, disposed on a distal side of said balloon and terminating in an aperture; and, d) at least one additional aperture in said unitary tube, disposed distally of said balloon, whereby during use said additional aperture diminishes the resistance in said unitary tube.

2. The endotracheal tube of claim 1 wherein said at least one additional aperture is disposed on said tapered distal portion.

3. The endotracheal tube of claim 1 wherein said tapered distal portion is generally configured similar to a mammalian nipple.

4. The endotracheal tube of claim 1 wherein said tapered distal portion is generally configured as a truncated conical section.

5. The endotracheal tube of claim 1 wherein said additional aperture is disposed partially on said tapered portion and partially on a constant cross-sectioned portion distal to said balloon.

* * * * *